US005604208A

United States Patent [19]
Alvarado-Licon

[11] Patent Number: 5,604,208
[45] Date of Patent: Feb. 18, 1997

[54] ANTIBIOTIC PREPARATION AND USE OF THE SAME IN PLANTS

[75] Inventor: Miguel E. Alvarado-Licon, Chihuahua, Mexico

[73] Assignee: Quimica Agronomica de Mexica, S.de.R.L.MI., Chihuahua, Mexico

[21] Appl. No.: 380,442

[22] Filed: Jan. 30, 1995

Related U.S. Application Data

[63] Continuation of Ser. No. 868,842, Apr. 16, 1992, abandoned.

[51] Int. Cl.$^6$ ..................................................... A61K 31/70
[52] U.S. Cl. ........................... 514/40; 514/152; 514/153; 514/154; 514/770; 536/13.6
[58] Field of Search ........................... 514/40, 152, 153, 514/154, 770; 536/13.6

[56] References Cited

U.S. PATENT DOCUMENTS 3,510,555   5/1970   Rogalski et al. ........................ 536/13.6

OTHER PUBLICATIONS

Mueller, *Chemical Abstracts*, vol. 72 (1970) No. 89255u.
Young et al, *Chemical Abstracts*, vol. 76(1972) No. 125826z.
Ionica, *Chemical Abstracts* vol. 78(1973) No. 119696g.
Chiykowski, *Chemical Abstracts* vol. 78(1973) No. 120075k.
Borges et al, *Chemical Abstracts*, vol. 80(1979) No. 671w.
Kassanis et al, *Chemical Abstracts*, vol. 85(1976) No. 29081t.
Dodds et al, *Chemical Abstracts*, vol. 95(1981) No. 112007a.
Eichholtz et al, *Chemical Abstracts*, vol. 96(1982) No. 99339j.
Kidd et al, *Chemical Abstracts*, vol. 97, (1982) No. 141500c.
Lee et al, *Chemical Abstracts*, vol. 106(1987) No. 170956r.
Acta Phytopapthologica Et Entomologica Hungarica, vol. 24, No. 3–4, 1989 Budapest, pp. 423–431, M. Scortichini et al.
Central Patents Index, Basic Abstracts Journal, Section Ch, Week 7214, 1972, Derwent Publications, Ltd., London, GB, Class C, AN 22821T & JP-A-7 211 000 (Japan Monopoly Corp.), Apr. 1972, abstract.
Chemical Abstracts, vol. 100, 1984, Columbus, Ohio, U.S., abstract No. 63358b & Egypt J. Microbiol. vol. 17, No. 1–2, 1983, pp. 65–80.
Chemical Abstracts, vol. 81, 1974, Columbus, Ohio, U.S., abstract No. 164535b. & Can. J. Plant Sci., vol. 54, No. 2, 1974, pp. 353–358.
Nigerian Journal of Pharmaceutical Sciences, vol. 2, No. 1, (1986), pp. 74–82.
Brochure—Gentamicin Plus, Mixture of Antibiotics for Agricultural Use, Wide Range Spectrum/Wettable Bactericide Powder.
Pamphlet—Agricultural Bactericide, Gentamicin Plus.

*Primary Examiner*—Elli Peselev
*Attorney, Agent, or Firm*—Sughrue, Mion, Zinn, Macpeak & Seas

[57] ABSTRACT

An antibiotic formulation comprising gentamicin, and optionally tetracycline or oxytetracycline, for use in plants.

25 Claims, No Drawings

ANTIBIOTIC PREPARATION AND USE OF THE SAME IN PLANTS

This is a continuation of U.S. patent application Ser. No. 07/868,842 filed Apr. 16, 1992, now abandoned.

FIELD OF THE INVENTION

The instant invention relates to an antibiotic preparation and use of the preparation in plants.

BACKGROUND OF THE INVENTION

Many plant varieties are subject to the devastating effects of bacterial infection. For example, fruit trees, such as pear and apple, are susceptible to a disease known as "Fire Blight". Plants infected during the bloom period experience damage to the flowers. Furthermore, the infected branch may die and/or the infection may spread, which can cause death of the tree. Ultimately there is a reduction of crop yield.

In the United States, there have been repeated reports of losses of fruit tree crops due to fire blight. While the losses are localized, the disease affects plants throughout the United States. Fire blight also has been noted in other countries such as New Zealand, Great Britain and Mexico. In those countries, affected crop plants include pear, apple, prune and quince. In most cases of fire blight outbreak, generally, entire trees are lost to the disease.

Once fire blight is diagnosed, the farmer is faced with the decision of destroying the infected trees to prevent further spread of the disease to other trees in the immediate area or treatment. It is known that fire blight is caused by a bacterium, *Erwinia amylovora*, and treatment thereof includes the spraying of trees with streptomycin. However, that treatment is ineffective.

It is of extreme importance that an efficacious and cost-effective treatment be devised for controlling or curing bacterial diseases of plants. The annual losses to the farmer are high and thus there is a need for a robust treatment for use in a wide variety of plants that remains simple to use.

SUMMARY OF THE INVENTION

It is an object of the instant invention to provide an anti-bacterial formulation for use in the treatment of bacterial infections in plants.

That and other objects have been obtained in the development of an anti-bacterial preparation comprising gentamicin, or salt thereof, as the active ingredient, or in another embodiment, comprising tetracycline or oxytetracycline, or salt thereof, and gentamicin, or salt thereof, that when suspended in an aqueous medium can be administered to a plant in any of a variety of ways, for example, by spraying.

DETAILED DESCRIPTION OF THE INVENTION

The antibiotic preparation of the instant invention comprises gentamicin, or salt thereof, as the active ingredient. In another embodiment, tetracycline or oxytetracycline, or salt thereof, and gentamicin, or salt thereof, are combined. In a preferred embodiment oxytetracycline hydrochloride and gentamicin sulfate are used. The antibiotic preparation of the instant invention is effective in controlling the growth of a wide range of microorganisms including, Erwinia species, Pseudomonas species, Xanthomonas species, Agrobacterium species and Corynebacterium species; in general, gram (−) species and even gram (+) species. Specific bacterial species include *Pseudomonas tabaci, P. angulata, P. lacrymans, P. phaseolitica, P. coronafaciens, P. pisi, P. delphinii, P. woodsii, P. marginalis, P. fluorescens, P. alliicola, P. cepacia, P. morsprunorum, P. gardeniae, P. solanacearum, P. caryophylli, P. glycinea, P. syringae, Xanthomona phaseoli* var. *sojensis, X. malvacearum, X. oryzae, X. translucens, X. oryzicola, X. pruni, X. vesicatoria, X. campestris, X. vasculorum, X. rubrilineans, X. citri, X. begoniae, X. gummisudans, X. pelargonii, X. juglandis, Corynebacterium insidiosum, C. flacumufaciens, C. sepedonicum, C. michiganense, Erwinia tracheifila, E. amylovora, E. carotovora* var. *chrysanthemi, E. stewartii, E. carotovora* var. *atroseptica, Agrobacterium tumefaciens, A. rhizogenes* and *A. rubi.*

The antibiotic preparation can be used in a wide variety of agriculturally beneficial species such as tobacco, vegetables including cucumber, the Cruciferae, pea and corn, beans such as soy beans, grains including cotton, rice, alfalfa, oat and other cereals, fruits, including apple, pear, peach, plum, tomato, banana, prune and citrus fruits, tubers and bulbs including potatoes and onions, nuts including walnut, grasses including sugar cane and the like.

The antibiotic preparation also is beneficial in the treatment of nursery plants and ornamental plants such as flowers, including chrysanthemum, begonia, gladiolus, geranium, carnations and gardenias.

The antibiotic preparation of the instant invention also finds use in the treatment of shade trees, forest trees, annual field crops and biannual field crops.

Other plant species in which the antibiotic preparation can be used are Espinas, Cotoneaster, Phyrachanthas, Stranvaesis, Fraxinus, Pyrus, Malus, Capsicum, Cydonia, Crataegus and Soreus.

For example, the antibiotic preparation of the instant invention can be used on *Amelanchier alnifolia, A. canadensis, A. laevia, Aronia arbutifolia, A. malanocarpa, Aruncus sylvester, Chaenomeles japonica, C. lagenaria, Cotoneaster acuminatus, C. adpressus Bois, C. affinis, C. ambiguus, C. apiculatus, C. ascendens, C. bullatus, C. bullatus f. floribunda, C. buxifolius, C. buxifolius f. vellaea, C. commixtus, C. congestus, C. conspicuus, C. dammeri, C. dielsianus, C. divaricatus, C. elegans, C. floccosus, C. foveolatus, C. franchetti, C. frigidus, C. glabratus, C. glaucophyllus, C. harrysmithii, C. henryanus, C. hissarcus, ignavus, C. insignia, C. horizontalis, C. khasiensis, C. lacteus, C. laxiflorus, C. lucidus, C. melanocarpus, C. microphyllus, C. moupinensis, C. multiflorus, C. nanshan, C. nitens, C. obscurus, C. obtusus, C. pannosus, C. perpusillus, C. polyanthemus, C. prostratus, C. racemiflorus, C. roseus, C. rotundifolius, C. rubens, C. salcifolius, C. simonsii, C. soongoricus, C. spendens, C. sternianus, C. tenuipes, C. tomentosus, C. veitchii, C. villosulus, C. wardii, C. X watereri, C. zabelii, Cowania stansburiana, Crataegomespilus dardarii, Crataegus arnoldiana, C. crusgalli, C. douglassi, C. flavellata, C. mollis, C. monogyna, C. oxyacantha, C. pedicellata, C. phaenopyrum, C. punctata, C. succulenta, C. uniflora, Cydonia oblonga, C. sinensis, Dichotomanthes tristaniaecarpa,* Dryas sp., *Eriobotrya japonica,* Exochorda sp., *Fragaria X ananassa, F. virginiana,* Geum sp., *Heteromeles arbutifolia, Holodiscus discolor, Kageneckia oblonga, Kerria japonica, Malus malus* spp., *Mespilus germanica, Osteomeles anthyllidifolia, Peraphyllum ramossissimum, Photinia deflexa, P. glabra, P. villona,* Physocarpus sp., Potentilia sp., Prinsepia sp., *Prunus alleghaniensis, P. armeniaca, P. avium, P. besseyi, P. cerasifera, P. dasycarpa, P. domestica, P. fremontii, P. ilicifolia, P. lusitanica, P. mume,*

*P. nigra, P. salicina, P. simonii, P. spinosa, P. triloba, Pyracantha angustifolia, P. atalantioides, P. coccinea, P. crenulata, P. crenulata* var. *kansuensis, P. fortuneana, P. koidzummi, P. rogersiana, Raphiolepia indica, P. umbellata, Rhodotypos scandens, Rosa blanda, R. multifora, R. rubiginosa, R. rubrifolia, Rubus idaeus, Salycopersicum esculentum, Solanum tuberosum, Sorbaria, Sorbus americana, S. aria, S. aucuparia, S. mougeotii, S. occidentalis, S. tianshanica, Spiraea cantoniensis, S. densiflora* and *S. vanhouteii.*

The instant invention comprises as the active ingredient, gentamicin, or salt thereof, such as the sulfate salt, at a final concentration of about 1–200 µg/ml, on a suitable agriculturally acceptable carrier, which in turn is suspended in an agriculturally acceptable diluent, such as water or a fertilizer solution.

In another embodiment, gentamicin, or salt thereof, in the final concentration range noted above, can be combined with tetracycline or oxytetracycline, or salt thereof, such as the hydrochloride. A preferred final concentration of the tetracycline or oxytetracycline is 1–350 µg/ml and a preferred final concentration of gentamicin when used in combination with tetracylcine or oxytetracycline is 1–100 µg/ml. In a more preferred embodiment, gentamicin sulfate is present at a final concentration of about 8 µg/ml and oxytetracycline hydrochloride is present at a final concentration of about 24 µg/ml.

The antibiotic(s) is mixed as a dry ingredient(s) with an inert agriculturally acceptable particulate dry carrier or diluent which provides a fine powdery formulation. The antibiotic can be obtained from any of a number of commercial sources. Generally, USP grade antibiotics are used. For example, gentamicin sulfate and oxytetracycline hydrochloride can be obtained from Algon Chemical Inc., Haworth, N.J. or ATZ Chemical Inc., New York City, N.Y.

A suitable diluent is Primex®. (A trademarked product of Proveedora De Plaguicidas Mexicanos, S.A., Bosque de Ciruelos No. 130, 3er Piso, Col. Bosques de las Lomas, Mexico) Primex® is a fine particulate of neutral pH with the characteristics of clay comprising primarily potassium, calcium, iron, aluminum, sodium, magnesium, silicates and carbonates. The agriculturally acceptable diluent is one that serves as a carrier for the low concentrations of antibiotic(s) which adheres to the particles. The dry diluent is one which readily suspends in suitable liquid diluents for administration to plants, such as water. The suspension assures even dispersion of an effective concentration(s) of the antibiotic(s).

The appropriate weight of gentamicin, or salt thereof, and when present of tetracycline or oxytetracycline, or salt thereof, and dry diluent are weighed and placed into a dust mixer such as a "V-type" dust mixer made of rolled stainless steel. The formula components are fed through ports and the mixer is operated at a speed of about 15 revolutions per minute. Upon addition of the starting compounds, mixing is commenced for a period of about 10 minutes. The final finished formulation can be placed into suitable airtight and watertight bags, such as a polyethylene bag of suitable capacity, and stored in a dry state at room temperature, or that recommended by the antibiotic(s) manufacturer.

Thus, 1–200 grams of gentamicin, or salt thereof, is mixed with an appropriate amount of an agriculturally acceptable carrier to yield 800 grams of antibiotic preparation. When tetracycline or oxytetracycline, or salt thereof, is used also, 1–350 grams of the same is added to the formulation with the appropriate adjustment in the amount of agriculturally acceptable carrier to yield 800 grams of antibiotic preparation.

In a preferred embodiment, 8 grams of gentamicin sulfate are mixed with 792 grams of an agriculturally acceptable carrier, such as Primex®, and in another preferred embodiment, 8 grams of gentamicin sulfate and 24 grams of oxytetracycline hydrochloride are mixed with 768 grams of an inert diluent, such as Primex®, to obtain an 800 gram aliquot of the finished antibiotic composition. The finished antibiotic composition is diluted in 1,000 liters of liquid diluent, such as water, for application to the plants.

To assure better adhesion of the liquid, for example in the case when the suspension is applied to the plant surface, about 1–2 liters of glycerin can be added to the final diluted liquid formulation.

The diluted formulation then is applied to the plant by any of a variety of art-recognized means. For example, the formulation can be applied to the plant surface by spraying. Alternatively, the solution can be introduced injectably into a plant, for example, with a syringe, applied as a solid fertilizer-like preparation for absorption by the roots at the base of a plant or a solution can be distributed at the base of a plant for root absorption. The formulation can be applied as soon as symptoms appear or prophylactically before symptoms appear. Applications can be repeated, preferably for another two-six treatments, at an interval of about six to eight days, depending on the climate and rainfall. The application interval can be shortened appropriately in the event of rain.

EXAMPLES

Certain aspects of the invention now will be described further in the following non-limiting examples. Unless otherwise indicated, all amounts are in relation to (w/v) or (w/w).

EXAMPLE 1

To determine the sensitivity of *Erwinia amylovora* to various antibiotics, a stock of *E. amylovora* was applied to commercially prepared agar-containing petri dishes comprising various antibiotics at known concentrations. An analogous commercially available system for making routine determinations of bacterial sensitivities and minimum inhibitory concentrations (MIC) of the relevant antibiotics using an ELISA format is the MicroScan® System distributed by Scientific Products of the Baxter Healthcare Corporation, McGaw Park, Ill. *E. amylovora* was found to be highly sensitive to gentamicin and less sensitive to oxytetracycline when each antibiotic was tested alone. An excellent effect was noted when gentamicin sulfate and oxytetracycline were combined and tested as to antimicrobial effectivness against *E. amylovora.*

EXAMPLE 2

The instant invention was tested against fire blight (*Erwinia amylovora*) in several apple and pear orchards. Orchard 1 comprised 8 year old Bartlett pears. Orchard 2 comprised 12 year old Golden Delicious apples. Orchard 3 comprised 16 year old Rome Beauty apples.

The experimental treatments included: 1) the instant invention, gentamicin sulfate (8 µg/ml) and oxytetracycline hydrochloride (24 µg/ml); 2) a comparison treatment, streptomycin sulfate (150 µg/ml) and oxytetracycline hydrochloride (15 µg/ml); and 3) controls, trees sprayed with water alone. Treatments were applied using a paperback sprayer and trees were sprayed until run off. In all orchards, sprays were timed to coincide with the fruit tree full bloom and petal fall and orchards were sprayed twice during the bloom period.

In all experimental orchards, treatments were arranged in a complete random block design to eliminate possible effects of orchard heterogeneity. There were four blocks per experiment, three treatments per block and five trees per treatment. Data were analyzed through a two-way ANOVA analysis using the statistical package, SYSTAT (SYSTAT: The system for statistics. Systat Inc. Evanson, Ill.). Prior to the ANOVA analysis, field data were transformed (sqr[y +0.5]) to reduce variance. Separation of treatment means was performed using Tukey's test (P<0.05) on transformed data.

Data collected at orchards 1 and 2 showed that the effect of the instant invention to prevent fire blight infection was highly significant (P<0.05). Compared to the use of streptomycin and tetracycline, the instant formulation controlled fire blight during critical period of infection in both pear and apple trees (Tables 1 and 2).

At orchard 3 the ANOVA analysis as well as the Tukey's test showed that while the instant invention was more effective than the formulation using streptomycin, there was no statistically significant difference between the instant invention and streptomycin treatments. However, the instant invention was statistically different (P=0.05) from the control (trees sprayed just with water) (Tables 3 and 4).

When submitted to Tukey's test, the mean number of buds infected by fire blight in the gentamicin treatments was significantly (P<0.5) less than that observed in streptomycin and control treatments (Table 4).

TABLE 1

Statistics for ANOVA analysis on the number of buds infected by fire blight on pear trees at Orchard 1.

| Source | Sum of Squares | df | Mean Square | F-Ratio | P |
| --- | --- | --- | --- | --- | --- |
| Treatments | 22.06 | 2 | 11.03 | 29.19 | 0.00 |
| Blocks | 1.31 | 3 | 0.44 | 1.16 | 0.33 |
| (Treatments × Blocks) | 2.28 | 6 | 0.37 | 0.98 | 0.45 |
| Error | 18.14 | 48 | 0.38 | | |

Durbin-Watson D Statistic 1.979
First order autocorrelation 0.006

TABLE 2

Statistics for ANOVA analysis on the number of buds infected by fire blight on apple trees at Orchard 2.

| Source | Sum of Squares | df | Mean Square | F-Ratio | P |
| --- | --- | --- | --- | --- | --- |
| Treatments | 24.66 | 2 | 12.33 | 50.36 | 0.00 |
| Blocks | 0.31 | 3 | 0.10 | 0.43 | 0.73 |
| (Treatments × Blocks) | 0.34 | 6 | 0.06 | 0.23 | 0.96 |
| Error | 11.75 | 48 | 0.24 | | |

Durbin-Watson D Statistic 1.797
First order autocorrelation 0.85

TABLE 3

Statistics for ANOVA analysis on the number of buds infected by fire blight on apple trees at Orchard 3.

| Source | Sum of Squares | df | Mean Square | F-Ratio | P |
| --- | --- | --- | --- | --- | --- |
| Treatments | 14.45 | 2 | 7.22 | 35.64 | 0.00 |
| Blocks | 0.85 | 3 | 0.28 | 1.41 | 0.25 |
| (Treatments × Blocks) | 1.48 | 6 | 0.24 | 1.21 | 0.31 |
| Error | 9.73 | 48 | 0.20 | | |

Durbin-Watson D Statistic 2.445
First order autocorrelation −0.237

TABLE 4

Statistics of the Tukey HSD multiple comparison on the mean number of fire blight infected buds per treatment.

| Treatment | Locality | | |
| --- | --- | --- | --- |
| | Namiquipa | Guerrero | Rubio |
| Oxytetracycline + Gentamicin | 0.25a | 0.70a | 1.35a |
| Streptomycin + Oxytetracycline | 2.05b | 2.30b | 1.95a |
| Control (Water) | 5.20c | 6.50c | 5.50b |

Values followed by the same letter are not significantly different at P = 0.05.

While the invention has been described with reference to specific examples and references herein, the skilled artisan will recognize readily that various modifications and embellishments can be made without departing from the spirit and scope of the instant invention.

What is claimed is:

1. A plant antibiotic composition comprising a bacteriostatically or bacteriocidally effective amount of gentamicin, or salt thereof, and an inert, agriculturally acceptable particulate carrier which suspends in an agriculturally acceptable liquid diluent, wherein said gentamicin adheres to the surface of said particulate inert, carrier.

2. The plant antibiotic composition of claim 1, further comprising a bacteriostatically or bacteriocidally effective amount of tetracycline or oxytetracycline, or salt thereof, wherein said tetracycline or oxytetracycline adheres to the surface of said inert, particulate carrier.

3. The plant antibiotic composition claim 1, wherein said inert, agriculturally acceptable particulate carrier is a silicate.

4. The plant antibiotic composition of claim 1, wherein said amount of gentamicin, or salt thereof, is about 0.125–25% (w/w).

5. The plant antibiotic composition of claim 2, wherein said amount of tetralcine or oxytetracycl ine, or salt thereof, is about 0.125–43.75% (w/w).

6. The plant antibiotic composition of any one of claims 1–5, wherein said composition is mixed with an agriculturally acceptable liquid diluent.

7. The plant antibiotic composition of claim 6, wherein said composition is mixed with water at a ratio of about 0.8 grams per liter of water.

8. The plant antibiotic of claim 1, wherein said amount is about 1% (w/w).

9. The plant antibiotic of claim 5, wherein said gentamicin is gentamicin sulfate in an amount of about 1% (w/w) and said tetracycline or oxytetracycline is oxytetracycline hydrochloride in an amount of about 3% (w/w).

10. A method of treating plants comprising exposing plants suspected of being infected with a pathogenic microorganism to a composition comprising a bacteriostatically or bacteriocidally effective amount of gentamicin, or salt thereof, and an inert, agriculturally acceptable particulate carrier which suspends in an agriculturally acceptable liquid diluent, wherein said gentamicin adheres to the surface of said inert, particulate carrier.

11. The method of claim 10, wherein said composition further comprises a bacteriostatically or bacteriocidally effective amount of tetracycline or oxytetracycline, or salt thereof, wherein said tetracycline or oxytetracycline adheres to the surface of said inert, particulate carrier.

12. The method of claim 10, wherein said inert, agriculturally acceptable particulate carrier is a silicate.

13. The method of claim 10, wherein said amount of gentamicin, or salt thereof, is about 0.125–25% (w/w).

14. The method of claim 11, wherein said amount of tetracycline or oxytetracycline, or salt thereof, is about 0.125–43.75% (w/w).

15. The method of any one of claims 10–14, wherein said composition is mixed with an agriculturally acceptable liquid diluent.

16. The method of claim 15, wherein said composition is mixed with water at a ratio of about 0.8 grams per liter of water.

17. The method of claim 13, wherein said amount is about 1% (w/w).

18. The method of claim 14, wherein said gentamicin is gentamicin sulfate in an amount of about 1% (w/w) and said tetracylcine or oxytetracycline is oxytetracycline hydrochloride in an amount of about 3% (w/w).

19. A plant antibiotic composition comprising a bacteriostatically or bacteriocidally effective amount of gentamicin, or salt thereof, an inert, agriculturally acceptable particulate carrier which suspends in an agriculturally acceptable liquid diluent and an agriculturally acceptable liquid diluent, wherein said gentamicin adheres to the surface of said inert, particulate carrier.

20. The plant antibiotic composition of claim 19, further comprising a bacteriostatically or bacteriocidally effective amount of tetracycline or oxytetracycline, or salt thereof, wherein said tetracycline or oxytetracycline adheres to the surface of said inert, particulate carrier.

21. The plant antibiotic composition of claim 19, wherein said concentration of gentamicin, or salt thereof, is about 1–200 μg/ml.

22. The plant antibiotic composition of claim 20, wherein said concentration of tetracycline or oxytetracycline, or salt thereof, is about 1–350 μg/ml.

23. The plant antibiotic composition of claim 21, wherein said concentration of gentamicin or salt thereof, is about 8 μg/ml.

24. The plant antibiotic composition of claim 22, wherein said concentration of tetracycline or oxytetracycline, or salt thereof, is about 24 μg/ml.

25. The plant antibiotic composition of claim 20, wherein said gentamicin is gentamicin sulfate in a concentration of about 8 μg/ml and said tetracycline or oxytetracylcine is oxytetracycline hydrochloride in a concentration of about 24 μg/ml.

* * * * *